United States Patent [19]
Sterling et al.

[11] Patent Number: 6,025,597
[45] Date of Patent: Feb. 15, 2000

[54] NON-INVASIVE INFRARED ABSORPTION SPECTROMETER FOR MEASURING GLUCOSE OR OTHER CONSTITUENTS IN A HUMAN OR OTHER BODY

[75] Inventors: Bernhard B. Sterling, Danville; James R. Braig, Alameda, both of Calif.; Daniel S. Goldberger, Boulder, Colo.; Charles E. Kramer, Poway, Calif.; Arthur M. Shulenberger, Brisbane, Calif.; Rick Trebino, Livermore, Calif.; Richard King, Berkeley, Calif.; Rogelio O. Herrera, Oakland, Calif.

[73] Assignee: Optiscan Biomedical Corporation, Alameda, Calif.

[21] Appl. No.: 08/957,309

[22] Filed: Oct. 23, 1997

Related U.S. Application Data

[63] Continuation of application No. 08/544,267, Oct. 17, 1995, abandoned.

[51] Int. Cl.[7] .................................................. G01N 21/71
[52] U.S. Cl. ................................ 250/341.6; 250/339.03; 250/339.12; 250/340
[58] Field of Search .......................... 250/341.6, 341.1, 250/330, 339.07, 339.03, 339.12, 340

[56] References Cited

U.S. PATENT DOCUMENTS

| | | | |
|---|---|---|---|
| 3,958,560 | 5/1976 | March . | |
| 4,223,680 | 9/1980 | Jobsis | 128/633 |
| 4,281,645 | 8/1981 | Jobsis | 128/633 |

(List continued on next page.)

FOREIGN PATENT DOCUMENTS

| | | | |
|---|---|---|---|
| 56-147045 | 11/1981 | Japan | 250/339.03 |
| 612271 | 7/1979 | Switzerland . | |
| WO8100622 | 3/1981 | WIPO . | |

OTHER PUBLICATIONS

Halliday et al., Fundamentals of Physics 2nd Edition, pp. 358–361, 1981.

R. Bowling Barnes, Thermography of the Human Body, American Association for the Advancement odf Science, vol. 140, No. 3569, pp. 870–877, May 24, 1963.

Barnes, Barnes Infrared Camera, Defense and Space Division Barnes Engineering Co. Bulletin 12–600, pp. 1–12, May 1, 1963.

Dueker et al. Germanium Nonscanned Infrared Imager, IEEE Transactions on Electron Devices, vol. ED–18, No. 11, pp. 1108–1112, Nov. 1971.

Dixon et al., Infrared Thermography of Subsurfaces Defects, Dow Chemical U.S.A, US Atomic Energy Commision Contract AR(29–1)–1106 pp. 73–77, Apr. 1972.

F. G. Pollack, Adbvances in Turbine Blade Temperature Measurements, 22nd International Instrumentation Symposium. San Diego, CA, ISA ASI 76256, pp. 393–398, May 1976.

(List continued on next page.)

Primary Examiner—Constantine Hannaher
Attorney, Agent, or Firm—Sawyer & Associates

[57] ABSTRACT

A noninvasive infrared spectrometer which includes an infrared detector system for measuring the intensity, wavelength, and time varying nature of infrared energy emanating from deep layers within a body. Before detection, the energy emanating from deep within the body passes through layers of that body in the presence of a natural or induced thermal gradient. The measured infrared energy is processed into an absorption spectra and then into a concentration of at least one constituent of the body which concentration may be strongly dependent on the depth into the body. In one embodiment the temperature gradient is induced by chilling the surface of the body to provide a clearer indication of the infrared absorption levels of the deeper constituents. Other embodiments describe the sequential or simultaneous heating and cooling of the heterogenous body to induce and capture the transient infrared absorption spectral information.

67 Claims, 8 Drawing Sheets

U.S. PATENT DOCUMENTS

| | | |
|---|---|---|
| 4,407,290 | 10/1983 | Wilber . |
| 4,429,999 | 2/1984 | Bimberg et al. .......... 250/341.6 |
| 4,655,225 | 4/1987 | Dahne et al. .............. 128/633 |
| 4,714,080 | 12/1987 | Edgar, Jr. et al. . |
| 4,819,752 | 4/1989 | Zelin . |
| 4,883,055 | 11/1989 | Merrick ...................... 128/633 |
| 4,934,372 | 6/1990 | Corenman et al. . |
| 5,009,230 | 4/1991 | Hutchinson . |
| 5,028,787 | 7/1991 | Rosenthal et al. . |
| 5,070,242 | 12/1991 | McClelland et al. ............ 250/339 |
| 5,070,874 | 12/1991 | Barnes et al. .............. 128/633 |
| 5,075,552 | 12/1991 | McClelland et al. .......... 250/341.6 |
| 5,077,476 | 12/1991 | Rosenthal .................... 250/341 |
| 5,081,998 | 1/1992 | Yelderman et al. . |
| 5,095,913 | 3/1992 | Yelderman et al. . |
| 5,137,023 | 8/1992 | Mendelson et al. . |
| 5,159,936 | 11/1992 | Yelderman et al. . |
| 5,191,215 | 3/1993 | McClelland et al. .......... 250/341.6 |
| 5,204,532 | 4/1993 | Rosenthal .................... 250/341 |
| 5,237,178 | 8/1993 | Rosenthal et al. ............. 250/341 |
| 5,267,152 | 11/1993 | Yang et al. ............... 364/413.09 |
| 5,277,181 | 1/1994 | Mendelson et al. ............ 128/633 |
| 5,313,941 | 5/1994 | Braig et al. ................. 128/633 |
| 5,342,789 | 8/1994 | Chick et al. ................. 436/501 |
| 5,355,880 | 10/1994 | Thomas et al. .............. 128/633 |
| 5,360,004 | 11/1994 | Purdy et al. ................. 128/633 |
| 5,361,758 | 11/1994 | Hall et al. ................... 128/633 |
| 5,370,114 | 12/1994 | Wong et al. ................. 128/633 |
| 5,372,135 | 12/1994 | Mendelson et al. ............ 128/633 |
| 5,372,136 | 12/1994 | Steuer et al. ................ 128/633 |
| 5,383,452 | 1/1995 | Buchert ....................... 128/633 |
| 5,451,787 | 9/1995 | Taylor ....................... 250/338.5 |
| 5,471,056 | 11/1995 | Prelat ........................ 250/334 |
| 5,473,162 | 12/1995 | Busch et al. ................ 250/341.6 |
| 5,477,051 | 12/1995 | Tsuchiya ................... 250/339.12 |

OTHER PUBLICATIONS

A. S. Glushkov, Thermoptical coverter with liquid modulating medium, Sov. Tech. Phys. Lett.5(10), p. 512, Oct. 1979.

Noninvasive Blood Glucose Measurement System as a Glucose Monitoring Device in an Artificial Endocrine Pancreas; H. Fukushima, et al., Department of Metabolic Medicine, Kumamoto University Medical School, 1990; pp. 38–42.

Glucose Spectra 10,000 mg/dl Glucose; Sigmoidal Glucose Gradient at 40 Microns

NON-INVASIVE INFRARED ABSORPTION SPECTROMETER FOR MEASURING GLUCOSE OR OTHER CONSTITUENTS IN A HUMAN OR OTHER BODY

This application is a continuation of application Ser. No. 08/544,267, filed Oct. 17, 1995, now abandoned.

FIELD OF THE INVENTION

The present invention relates to an instrument and a method for noninvasively measuring the concentration of a constituent or constituents in a body. In particular, the present invention relates to an instrument for monitoring the infrared absorption of such constituents at prescribed depths in the body and at infrared wavelengths where the constituents have distinguished absorption spectra. The measurement and processing, including quantification of the constituents, is made by measuring, in a time/depth dependent manner, the specific infrared absorption of the constituents of interest by monitoring the infrared energy band naturally emitted from the body in the presence of a natural or induced temperature gradient.

BACKGROUND OF THE INVENTION

Infrared spectrometry is an accepted and widely practiced technique for identification and quantification of compounds. The most common method of analysis is via a transmission spectra. In this method an analysis beam of infrared light is passed through the substance being analyzed. The sample substance absorbs light in varying amounts at different wavelengths producing a transmission spectra which is a graph of the energy passed through the sample vs. wavelength. In this method the substance being analyzed is contained in a "cell" and placed inside the instrument for scanning. The analysis beam enters one side of the cell and exits the other. This is clearly an in-vitro technique not suitable for non-invasive measurements.

In another common technique the phenomena of Attenuated Total Internal Reflection (ATIR) is used. In this technique the sample is deposited on a plate fabricated of infrared transmissive material. The analysis beam is reflected off of this plate and back into the analyzer. At the point of reflection a portion of the analysis beam (evanescence wave) actually travels through the plate and interacts with the sample, then this portion of the beam returns to the analyzer along with the other reflected beam. A 1000 cm–1 infrared ATIR beam typically penetrates 10 microns into the sample under study. This technique, although potentially noninvasive, is not suitable for studying the composition of deeper layers of a material.

Transmission mode measurements are ideal for gasses which transmit a large percentage of incident energy and can be easily contained in a cell. Solids and liquids are traditionally measured by using either very thin transmission mode samples or the ATIR technique. The transmission mode technique has severe limitations if the substance being measured is very dense in the wavelength region of interest.

For instance if one was analyzing glucose dissolved in water or human blood the 9 to 10 micron wavelength region would be ideal however the incident analysis beam would be totally absorbed with less than 200 microns of path length. Maintaining a sample of such thin proportions is difficult. In such a case of high absorption, the ATIR technique might be useful, however, in that technique the analysis beam passes only approximately 10 microns into the substance being analyzed. The technique is useful only if the properties being measured exist very near the surface of the sample.

The transmission and ATIR mode analysis are very useful in the laboratory however if one wishes to measure something in-vivo such as glucose in blood where the most peripheral capillaries are covered by typically 40 microns of epithelial tissue clearly neither techniques are adequate.

Infrared detection techniques are widely used for the calculation of oxygen saturation and the concentration of other blood constituents. For example, noninvasive pulse oximeters have been used to measure absorption signals at two or more visible and/or near infrared wavelengths and to process the collected data to obtain composite pulsatile flow data of a person's blood. Sample pulse oximeters of this type are described by Corenman et al. in U.S. Pat. No. 4,934,372; by Edgar, Jr. et al. in U.S. Pat. No. 4,714,080; and by Zelin in U.S. Pat. No. 4,819,752.

Infrared detection techniques have also been used to calculate the concentrations of constituents such as nitrous oxide and carbon dioxide in the expired airstream of a patient. For example, Yelderman et al. describe in U.S. Pat. Nos. 5,081,998 and 5,095,913 techniques for using infrared light to noninvasively measure the absolute concentrations of the constituents of the respiratory airstream of a patient by placing an infrared transmission/detection device on the artificial airway of the patient. These infrared detection techniques and those described above have proven to be quite accurate in the determination of arterial blood oxygen saturation, the patient's pulse, and the concentrations of carbon dioxide, nitrous oxide and other respiratory constituents.

Spectrophotometric methods have also been used to noninvasively monitor the oxidative metabolism of body organs in vivo using measuring and reference wavelengths in the near infrared region. For example, Jobsis describes in U.S. Pat. Nos. 4,223,680 and 4,281,645 a technique in which infrared wavelengths in the range of 700–1300 nm are used to monitor oxygen sufficiency in an organ such as the brain or heart of a living human or animal. In addition, Wilber describes in U.S. Pat. No. 4,407,290 a technique in which visible and near infrared light emitting diodes and detection circuitry are used to noninvasively measure changes in blood thickness of predetermined blood constituents relative to total change in blood thickness at a test area so as to determine the concentration of such constituents in the blood. Such constituents include hemoglobin and oxyhemoglobin, and the measured concentrations are used to determine the oxygen saturation of the blood. Wilber further suggests at columns 11–12 that such techniques may be extended to the measurement of glucose in the bloodstream; however, Wilber does not tell how to make such measurements, what wavelengths of energy to use, or the form of the mathematics necessary for the calculation of glucose concentration.

Long wavelength spectroscopic glucose monitoring techniques using infrared light are presently believed to be the most accurate and are the subject of the present application. Unlike the noninvasive oxygen saturation measurement techniques described above, prior art spectroscopic glucose monitoring techniques have typically used extra-corporeal "flow through" cells that allow continuous measurements using infrared light. Indeed, attenuated total internal reflection (ATIR) cells have been employed in the long wavelength infrared to measure the glucose content of extracted blood samples. However, such techniques require samples of blood to be taken from the person and are thus undesirable for widespread consumer use.

Laser Raman Spectroscopy is another spectroscopic technique which uses a visible spectrum range stimulus and the visible red spectrum for measurement. As with ATIR cells, extra-corporeal blood is also used with Raman Technology. The Raman technique is based upon the principle that if excited with a specific wavelength certain constituents will re-emit optical energy at composition dependent specific wavelengths. Over the entire visible spectrum range whole blood has a high degree of absorption.

Another class of spectroscopic technique is described by Barnes in U.S. Pat. No. 5,070,874. According to this technique, often referred to as noninvasive near infrared spectroscopy, light is passed though a finger or suitable appendage and monitored upon exit for measuring glucose levels in vivo. Unfortunately, this technique suffers from two sources of inaccuracy: tissue interference and lack of specificity. Moreover, while the near infrared wavelengths used are easily and economically generated by light emitting diodes (LEDs) and solid state lasers, and easily transmitted through human tissue, they are not in a range specifically absorbed by glucose. This lack of "fingerprint" absorbance and interference from tissue pigment and condition render the technique unsuitable for accurate concentration determination but possibly acceptable for trending if stability can be maintained.

In an attempt to overcome the limitations of near infrared wavelengths Kaiser describes in Swiss Patent No. 612,271 a technique in which a high power infrared laser is used as the radiation source for measuring glucose concentration in a measuring cell. The measuring cell consists of an ATIR measuring prism which is wetted by the person's blood and an ATIR reference prism which is wetted with a comparison solution. $CO_2$ laser radiation, typically at 10.5 microns wavelength, is led through the measuring cell and gathered before striking a signal processing device. A chopper placed before the measuring cell allows two voltages to be obtained corresponding to the signal from the sample and the reference prisms.

Due to absorption corresponding to the concentration of the substance measured in the blood, the difference between the resulting voltages is proportional to the concentration. Unfortunately, the infrared laser used by Kaiser needs to be very powerful to get the 10.5 micron energy to pass through the blood and has the undesirable side effect of heating the blood, which may be harmful to the person if the blood were returned to the body. Although Kaiser suggests that over heating the blood may be prevented by using extra-corporeal cuvettes of venous blood and high blood flow rates, Kaiser does not describe a noninvasive technique for measuring glucose concentration.

March in U.S. Pat. No. 3,958,560 describes a "non invasive" automatic glucose sensor system which senses the rotation of polarized near infrared light which has passed through the cornea of the eye. March's glucose sensor fits over the eyeball between the eyelid and the cornea and measures glucose as a function of the amount of radiation detected at the detector on one side of the person's cornea. Unfortunately, while such a technique does not require the withdrawal of blood and is thus "noninvasive", the sensor may cause considerable discomfort to the person because of the need to place it on the person's eye. A more accurate and less intrusive system is desired.

Hutchinson describes in U.S. Pat. No. 5,009,230 a personal glucose monitor which also uses polarized near infrared light to noninvasively detect glucose concentrations in the person's bloodstream. The amount of rotation imparted on the polarized light beam is measured as it passes through a vascularized portion of the body for measuring the glucose concentration in that portion of the body. Although the monitor described by Hutchinson need not be mounted on the person's eye, the accuracy of the measurement is limited by the relatively minimal and non specific absorption of glucose in the 940–1000 nm range, dictated by the requirement of polarization, used by Hutchinson.

Mendelson et al. in U.S. Pat. No. 5,137,023 also found that wavelengths in the near infrared range are useful for noninvasively measuring the concentration of an analyte such as glucose using pulsatile photoplethysmography. In particular, Mendelson et al. describes a glucose measuring instrument which uses the principles of transmission and reflection photoplethysmography, whereby glucose measurement is made by analyzing either the differences or the ratio of two different near infrared radiation sources that are either transmitted through an appendage or reflected from a tissue surface before and after blood volume change occurs in the systolic and diastolic phases of the cardiac cycle. The technique of photoplethysmography can thus be used to adjust the light intensity to account for errors introduced by excessive tissue absorptions. However, despite the assertions by Mendelson et al., the wavelengths in the near infrared (below 2500 nm) are not strongly absorbed by glucose yet are susceptible to interference from other compounds in the blood and thus cannot yield sufficiently accurate measurements.

Rosenthal et al. in U.S. Pat. No. 5,028,787 disclose a noninvasive blood glucose monitor which also uses infrared energy in the near infrared range (600–1100 nm) to measure glucose. However, as with the above-mentioned devices, these wavelengths are not in the primary absorption range of glucose and, accordingly, the absorption at these wavelengths is relatively weak. A more accurate glucose measuring technique which monitors glucose absorption in its primary absorption range is desirable.

As with other molecules, glucose more readily absorbs infrared light at certain frequencies because of the characteristic and essential infrared absorption wavelengths of its covalent bonds. For example, as described by Hendrickson et al. in *Organic Chemistry*, 3rd Edition, McGraw-Hill Book Company, Chapter 7. Section 7-5, pages 256–264, C-C, C-N, C-O and other single carbon bonds have characteristic absorption wavelengths in the 6.5–15 micron range. Due to the presence of such bonds in glucose, infrared absorption by glucose is particularly distinctive in the far infrared. Despite these characteristics, few have suggested measuring glucose concentration in the middle to far infrared range, likely due to the strong tissue absorption that would attenuate signals in that range.

In one known example of such teachings, Mueller describes in WO 81/00622 a method and device for determining the concentration of metabolites in blood using spectroscopic techniques for wavelengths in the far infrared range. In particular, Mueller teaches the feasibility of measuring glucose in extra-corporeal blood samples using a 9.1 micron absorption wavelength and a 10.5 micron reference wavelength for stabilizing the absorption reading. However, Mueller does not describe how such wavelengths may be used in vivo to measure glucose concentration noninvasively while overcoming the above-mentioned tissue absorption problems. Without overcoming the large absorption by tissue in the 9 to 10 micron wavelength range, typically 90% absorption within 30 micron of optical path in human tissue, high power infrared energy must be incident on the measurement site which can cause tissue damage and discomfort.

On the other hand, infrared emissions of bodies have been used to determine the absolute temperatures of those bodies.

For example, some of the present inventors disclose a tympanic thermometer in U.S. Pat. No. 5,159,936 which measures the absolute temperature of a person from the sum total of all infrared energy emissions from the person's tympanic membrane. However, such broadband infrared energy emissions have not been used to perform constituent composition and concentration analysis.

McClelland in U.S. Pat. No. 5,070,242, U.S. Pat. No. 5,075,552, and U.S. Pat. No. 5,191,215 describes a method for applying a cooling medium to cool a thin surface layer portion of the material and to transiently generate a temperature differential between the thin surface layer portion and the lower portion of the material sufficient to alter the thermal infrared emission spectrum of the body from the black-body thermal infrared emission of the material. The altered thermal emission spectrum is detected while the emission spectrum is sufficiently free of self-absorption by the material of the emitted infrared radiation. The detection is effected prior to the temperature differential propagating into the lower portion of the material to an extent such that the altered thermal infrared emission spectrum is no longer sufficiently free of self-absorption by the material of emitted infrared radiation. By such detection, the detected altered thermal infrared emission spectrum is indicative of the characteristics relating to the molecular composition of the homogenous material.

Another prior art device developed by some of the same inventors is disclosed in U.S. Pat. No. 5,313,941 by Braig et al. In this device high intensity infrared energy of the optimal wavelength, 3 to 12 microns is passed through the finger to make a transmission mode measurement. This device requires high incident energy levels to overcome the high absorbance of tissue in this wavelength band. In this device the energy is pulsed at very low duty cycles to avoid overheating the skin.

A technique for the non invasive measurement of physiological constituents, specifically glucose, must address the problems that tissue is heterogeneous in composition with the tissue layers containing the physiological concentration of interest laying 40–150 microns below the surface. Furthermore, the technique must assure a safe and effective measurement that will not cause temporary or permanent damage to the surface or underlying tissues in the measurement site nor cause discomfort to the human subject. The technique must also overcome the potential problem that glucose and other physiological constituents are present in combination with a number of other similar molecules and must be distinguished for accurate quantification. Ideally such a technique would not require a high power source of infrared energy so that a device could be made portable and lightweight.

Accordingly, what is needed is a system and method to overcome the problems associated with prior art techniques and address the constraints cited above. The present invention addresses such a need.

SUMMARY OF THE INVENTION

The present invention provides an apparatus and technique that will allow the noninvasive measurement of substances in vivo. In addition to measuring glucose and other substances in tissue and human blood the invention may be useful for analyzing the composition of agricultural and pharmaceutical or any integral products without destruction and for measuring the contents of packaged goods without compromising the package seal.

It is an object of the present invention to use the infrared energy self absorption of the heterogenous sample as a source of the information used for analysis.

The optical subsystems of the present invention yield infrared transmission spectra from progressively deeper layers below the surface of the substances under test. The signal processing and computational subsystem of the present invention convert this spectral information into identity and concentration of compounds for which it is programmed.

DETAILED DESCRIPTION OF THE DRAWINGS

The present invention relates to the measurement of infrared energy absorption in a heterogeneous body. The following description is presented to enable one of ordinary skill in the art to make and use the invention as provided in the context of a particular application and its requirements. Various modifications to the preferred embodiments will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

Any object at a temperature above absolute zero (−273.16 Degrees Celsius) emits infrared energy. The energy density of such emissions is described by Planck's law:

$$W = em * Fn(u,t)$$

Where:

W=energy in Watts/cm^2 per micron
em=emissivity
Fn=a mathematical Function with variables u and t
u=wavelength of emitted energy, in microns
t=temperature of emitting body, in Kelvins
The full form of this equation is:

$$W = em * (3.74E4 / \{u^5 * [(exp(1.438E4/(u*t)) - 1]\})$$

Figure 1:
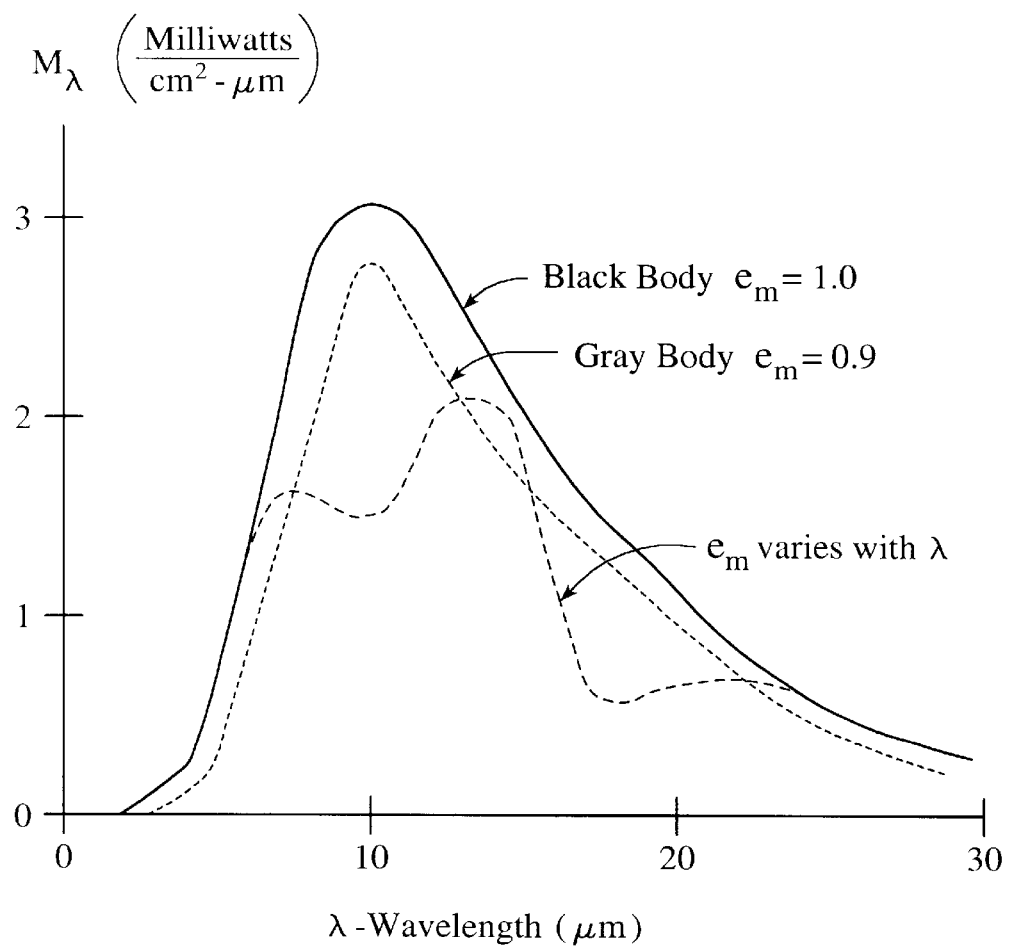
FIG. 1 is a block diagram of a black body emission spectra from a heated body.

The graph of these emissions vs. wavelength is often referred to as a blackbody curve. Such a curve is shown in FIG. 1. Theoretically, a body with emissivity 1.0 would exhibit this emission spectra according to Planck's law.

Many objects have emissivities close to 1.0. Human tissue for instance has an emissivity of approximately 0.9 to 0.98. It is well known that infrared emissions from the human body obey Planck's law and yield a black body type emission spectra.

Although a human body may emit energy that follows Planck's law, Planck's law does not completely describe the sum total of all energy emitted from a human body for two reasons:

1. The layers of the tissue and body fluids are selectively absorptive to some wavelengths of infrared energy. Thus layers of tissue and blood or other fluids may selectively absorb energy emitted by the deeper layers before that energy can reach the surface of the skin.

2. There is a temperature gradient within a body, the deeper layers being warmer than the outer layers which causes further deviation from the theoretical black body emissions.

Whenever these two conditions exist naturally, or can be forced to exist, Applicants have discovered that a composition dependent absorption spectra can be constructed from proper analysis of the total energy emitted from the body. For heterogeneous bodies, composition may be depth dependent and conversely, absorption spectra generated from deeper layers can contain sufficient composition information to allow quantification of the concentrations of individual constituents at that depth into the tissue. This is possible when a temperature gradient either occurs or is induced in the body. The slope of the temperature gradient is such that the temperature is cooler at the surface of the body closer to an infrared detector than at a more distant location from the detector, typically deep within the body.

The present invention uses the natural temperature within the body as the source of the infrared emissions. The natural emissions of the present invention are merely black body emissions fitting Planck's equation—they do not contain any composition dependent structure. As will be explained in more detail below as these deep infrared emissions pass through layers of tissue that are at a lower temperature than the deeper emitting layer they are selectively self absorbed. This selective self absorption produces bands of reduced energy in the resulting emission spectra when the energy finally exits the material under study. The spectra containing the bands where energy has been self absorbed is called an absorption spectra.

The present invention employs cooling to promote "self-absorption" by letting the temperature gradient propagate to selected layers typically between 40 and 150 microns below the surface. When the temperature gradient has sufficiently propagated, the present technique can, noninvasively, deliver absorption spectra of the tissue, blood, and interstitial fluid containing glucose. The present invention can deliver precise information about the composition of individual layers deep within a heterogeneous body of material by measuring the absorption spectra at different times as a temperature gradient propagates from the surface to deep within the material under test.

A conceptual explanation for the phenomenon in accordance with the present invention will be described herein below. Consider for the sake of explanation the case of human skin. It is known that in a typical forearm the core temperature is approximately 37 Deg. C. and the external surface is typically at 30 Deg. C.

Figure 2:
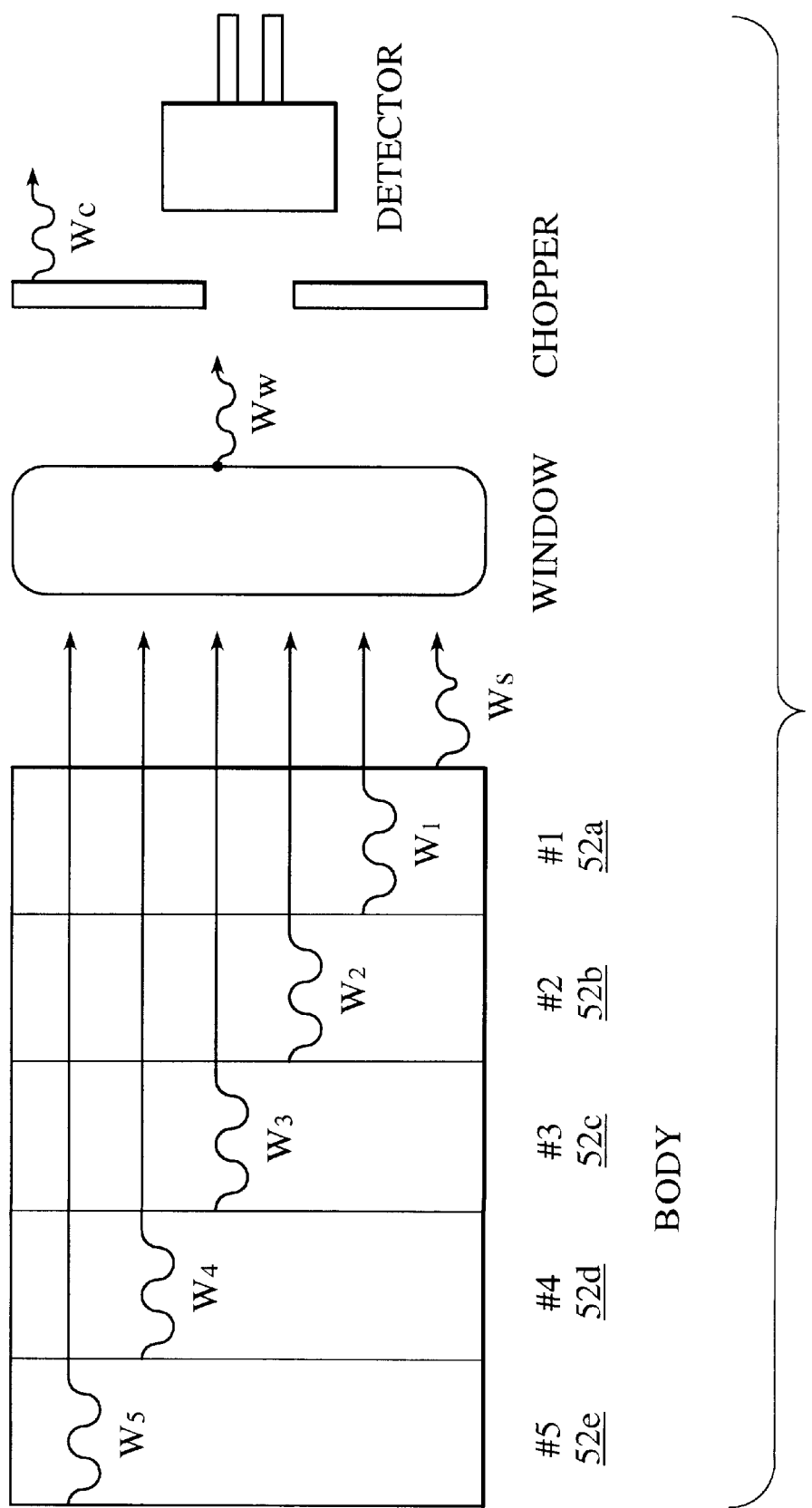
FIG. 2 is a block diagram of a typical body that includes multiple layers.

To simplify our conceptual model consider that the skin is made of many layers each approximately 10 microns thick. Let's further simplify our model in FIG. 2 by assuming that each layer 52a–52e in the model emits energy according to Planck's equation based on the temperature of that layer 52a–52e. A detector system 54 looking from outside can observe that radiation. The outermost layer 52a emits energy that travels directly to the detector 54, energy from the outer layer 52a does not pass through any other layer 52b–52e on its route to the detector 54. Energy from the second layer 52b inward must pass through the first layer 52a before exiting the tissue and passing on to the detector 54. As the energy from the second layer 52b enters the first layer 52a it is selectively absorbed by the compounds present in the first layer 52a. This absorption is just like the absorption that takes place in the classical transmission cell spectroscopy apparatus. The first layer 52a absorbs the energy from the second layer 52b selectively—at specific wavelengths.

The total energy radiated from the subject appears very much like conventional black body emissions. However, if careful observation is made the difference between a black body emission spectra and the emissions after absorption by deeper layers when an internal temperature gradient exists, subtle but important differences can be observed. The model of FIG. 2 was implemented using typical numbers and produced the output shown in FIGS. 3a and 3b.

Figure 3A:
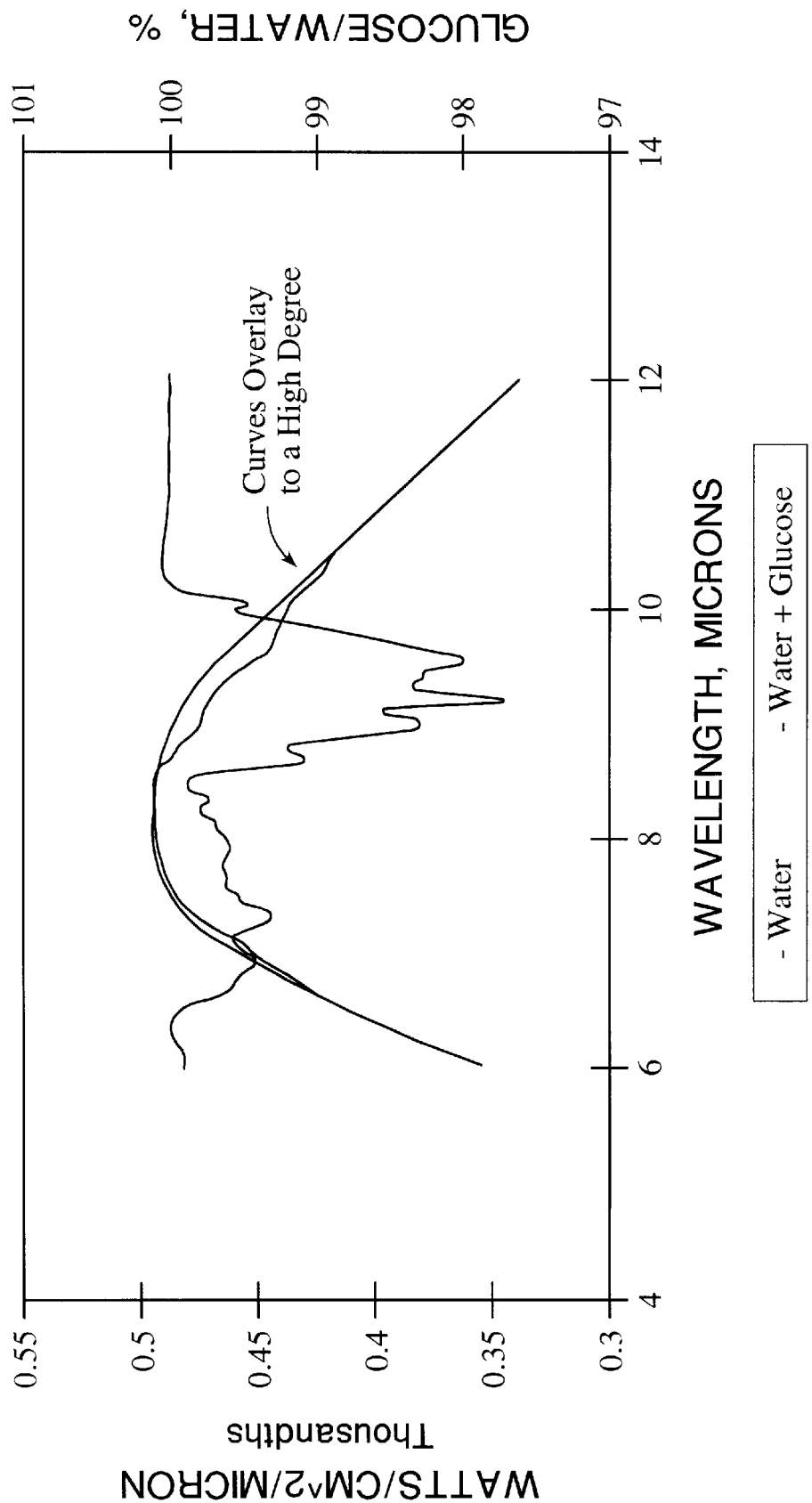
FIG. 3a is a diagram of an absorption spectrum of a constituent in a body, when the body has a thermal gradient.
Figure 3B:
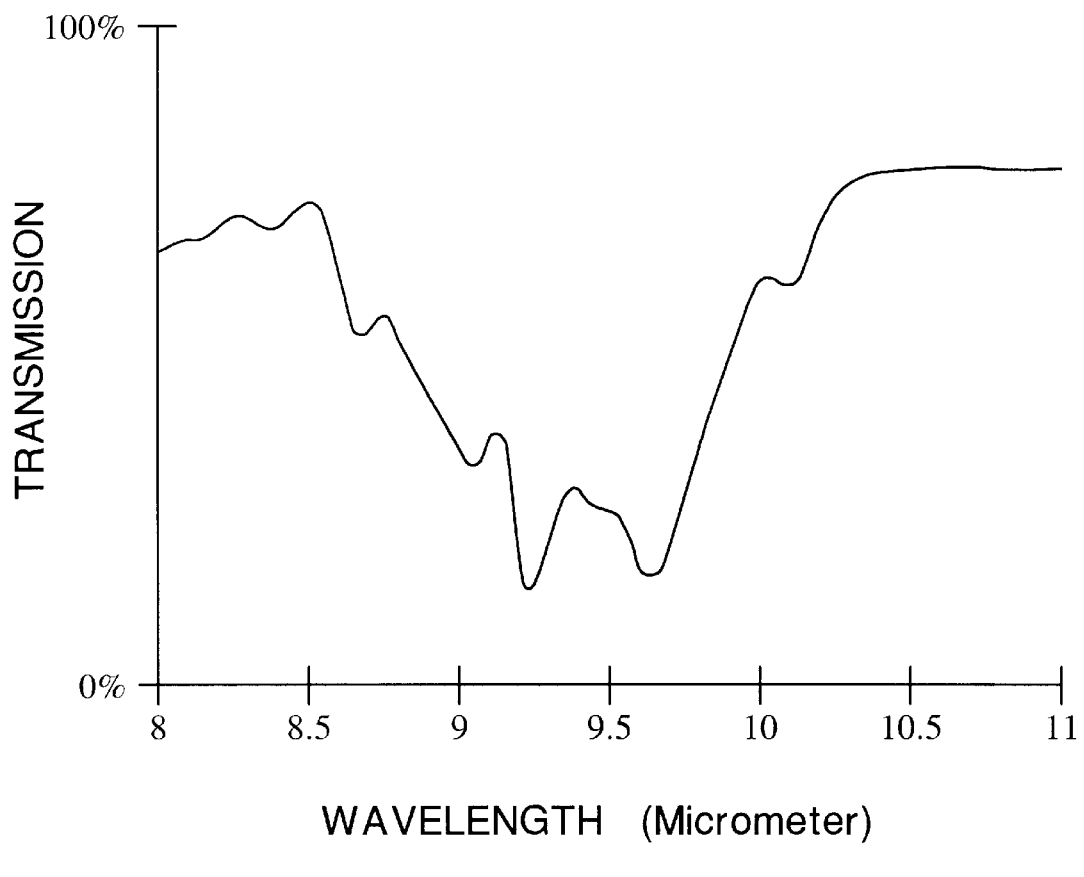
FIG. 3b is an absorption spectra of glucose produced using conventional transmission spectroscopy

With this model, for illustrative purposes two spectra are shown FIG. 3a, one for water and one for water with glucose dissolved in it. In normal physiological concentrations of glucose both spectra would look very similar to the Planck emission curves describing a black body and would be nearly overlapping. However, with high concentrations of glucose in solution (5%) a small perturbation near 9 microns can be observed. When the ratio of the glucose solution to the pure water emission spectra are taken the characteristic glucose absorption spectra emerges. The magnitude of the spectra depends on the glucose concentration and the temperature gradient. The gradient induced glucose spectra compares favorably with the conventional transmission spectra of glucose shown in FIG. 3b.

In order to elucidate spectral absorption of constituents of bodies where the presence and concentration of the constituent varies by depth below the surface it is necessary to establish and control the magnitude, propagation velocity and contour profile of the thermal gradient described previously. The above-identified model addressed only the absorption of layers of homogeneous material subjected to a large steady state thermal gradient. One purpose of this invention is to dynamically establish and control the magnitude and propagation depth of a thermal gradient to elucidate selectively (as a function of time and depth) the thermal absorption of the deeper layers below the surface within which the concentration of the tissue constituent is of physiological interest.

Figure 4:
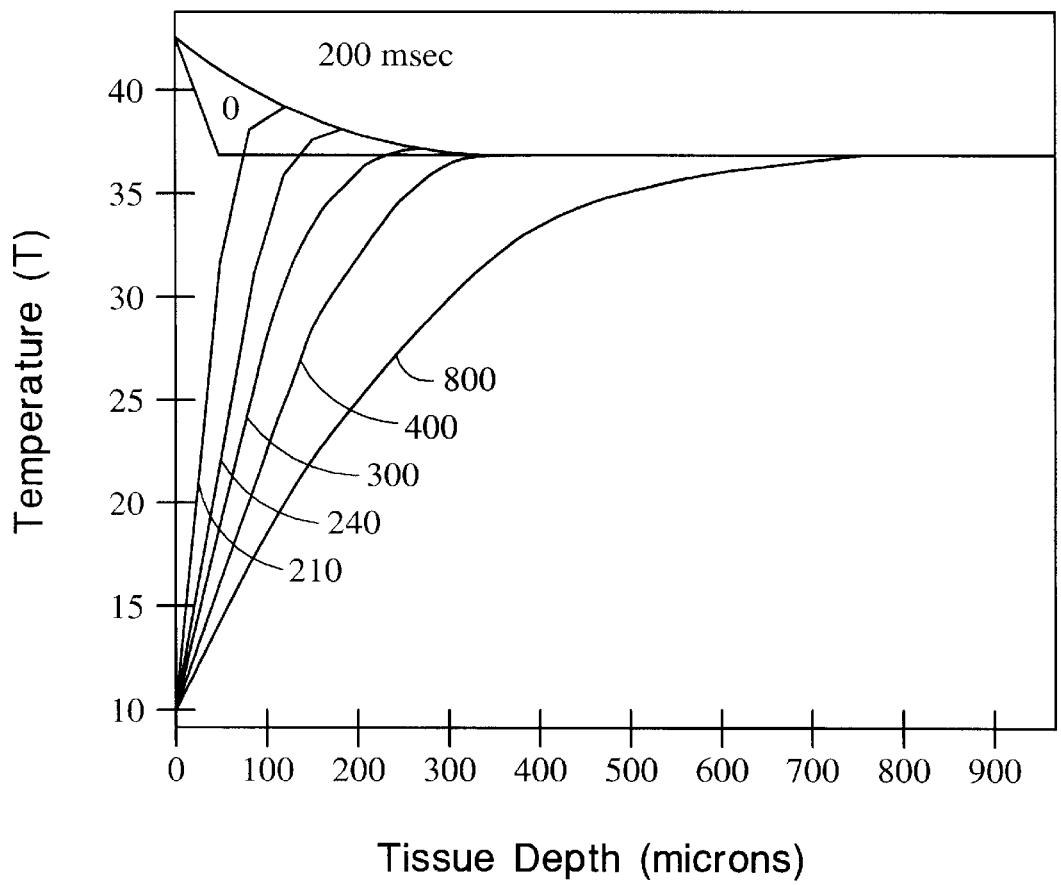
FIG. 4 is a curve that shows the influence of the gradient interacting with time/depth dependent constituents of interest.

The infrared spectral content of absorption by subsurface layers will be directly related to the magnitude of the gradient existing across the layer. The magnitude of the gradient will vary from near zero before the thermal gradient has propagated to that layer to a maximum value approximately defined by the difference between the high temperature within the body and the low temperature at the surface of the body divided by the thermal gradient depth. FIG. 4 also describes the three variables of the dynamics associated with the time dependency of establishment, propagation and thermal gradient contour profile induced into a body. FIG. 4 describes the influence of the gradient interacting with depth dependent concentrations of the constituents of interest, and FIG. 5 the corresponding infrared spectral absorption pattern. The thermal gradient contour profile is a three dimensional representation of the above concepts.

Figure 5:
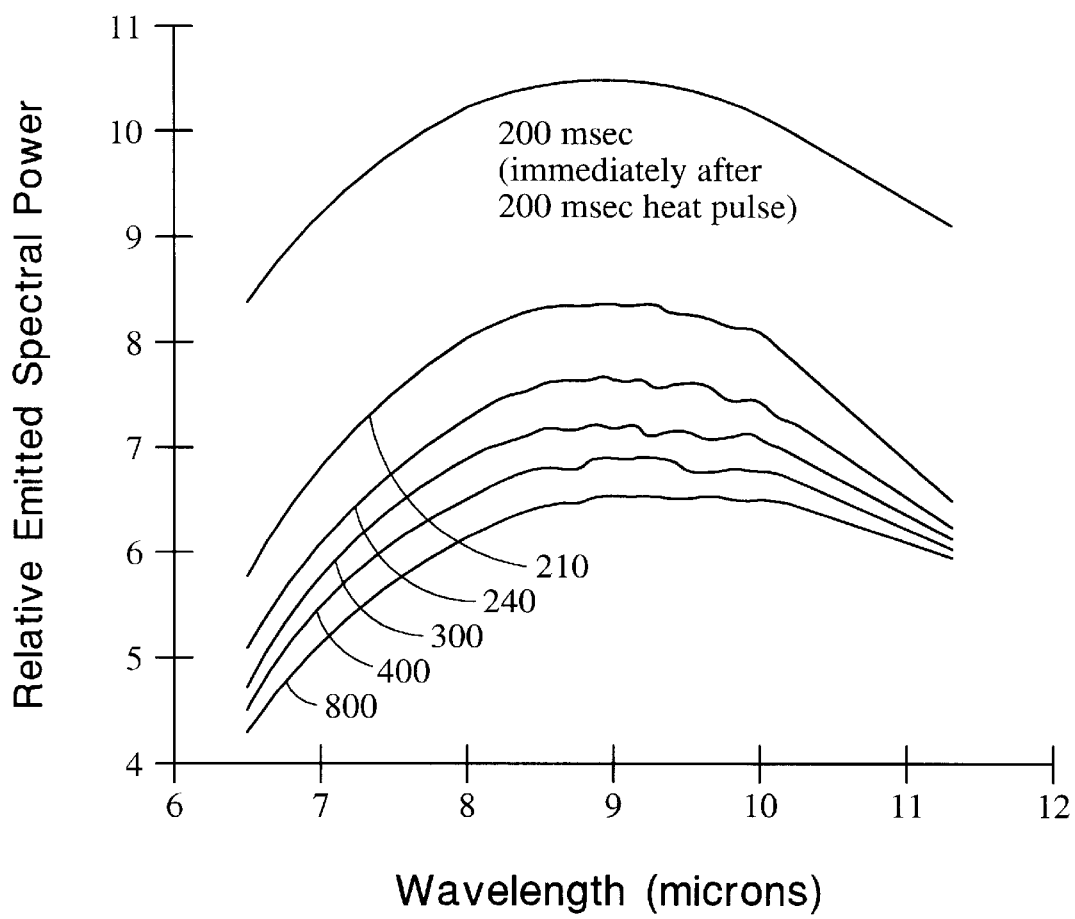
FIG. 5 is a curve which illustrates the time dependency of the spectral content of the absorption pattern.

The resultant time (depth) dependency of the spectral information, shown in FIG. 5, illustrates that in human tissue the spectral content of interest will not begin to appear in the infrared absorption until approximately 100 ms (milliseconds) after cooling the external surface has begun and will transiently increase in intensity with a maximum occurring between 125 to 175 ms. After which the spectral content will decrease until approximately 200 ms. The decrease is due to the accumulative effects of both optical absorption as a function of increasing depth and to the change in its profile (the decrease in the magnitude of the gradient).

In order to optimize the thermal gradient in magnitude, propagation velocity, and contour profile, the thermal boundary conditions and thermal conductive properties of the means for heating and cooling the body must be considered. The considerations are particularly important for physiological application of the invention wherein the body refers to the human body and avoidance of temporary or permanent damage to the tissue is paramount. The maximum temperature to which human tissue can be subjected for prolonged or repeated exposure is 41–42 Deg. C. The minimum temperature is less well defined but estimated at −3 Deg. C for transient exposure of 1–2 seconds.

The mechanism or process for creating and controlling the magnitude, propagation velocity and contour profile of the thermal gradient incorporates cyclic cooling and re-warming of the observation site. The mechanism or process for cooling the surface of the tissue target site is unique in the present invention in that the cooling body becomes part of the optical pathway through which the infrared energy must pass in order to be recorded.

For comfort of the subject upon whom the measurement is being made, it has been determined that the surface areas being heated and cooled should be approximately equal in size and approximately 1.91 cm in diameter. To improve the S/N in the measurement it is advisable to repeatedly observe the depth selective spectral emissions. The mechanical device designed to repetitively and repeatably cool and re-heat the target tissue area provides the capability to rapidly cycle between heating and cooling with a typical cycle time of 5 seconds.

Uniformity of the heating and cooling across the surface area of the target tissue and within the volume under the target site is also an important parameter for maximizing the spectral signal content of the depth dependent emissions. Reduced uniformity of the temperature across the surface during either heating or cooling will result in the thermal gradient profile not being uniform in a direction perpendicular to the surface. The resulting absorption spectra will contain absorption information from differing depths across the surface of the target thus loosing specificity between spectral content change and depth.

Quantifying the Amount of Constituent Present

Quantification of the substances of interest is derived from the relative energy emitted through a gradient enhancement technique. To quantify the amount of the substance of interest, a ratio method employs the relative energy emitted at a wavelength known to be absorbed by that substance normalized by the absorption at one or more reference wavelengths.

Figure 6:
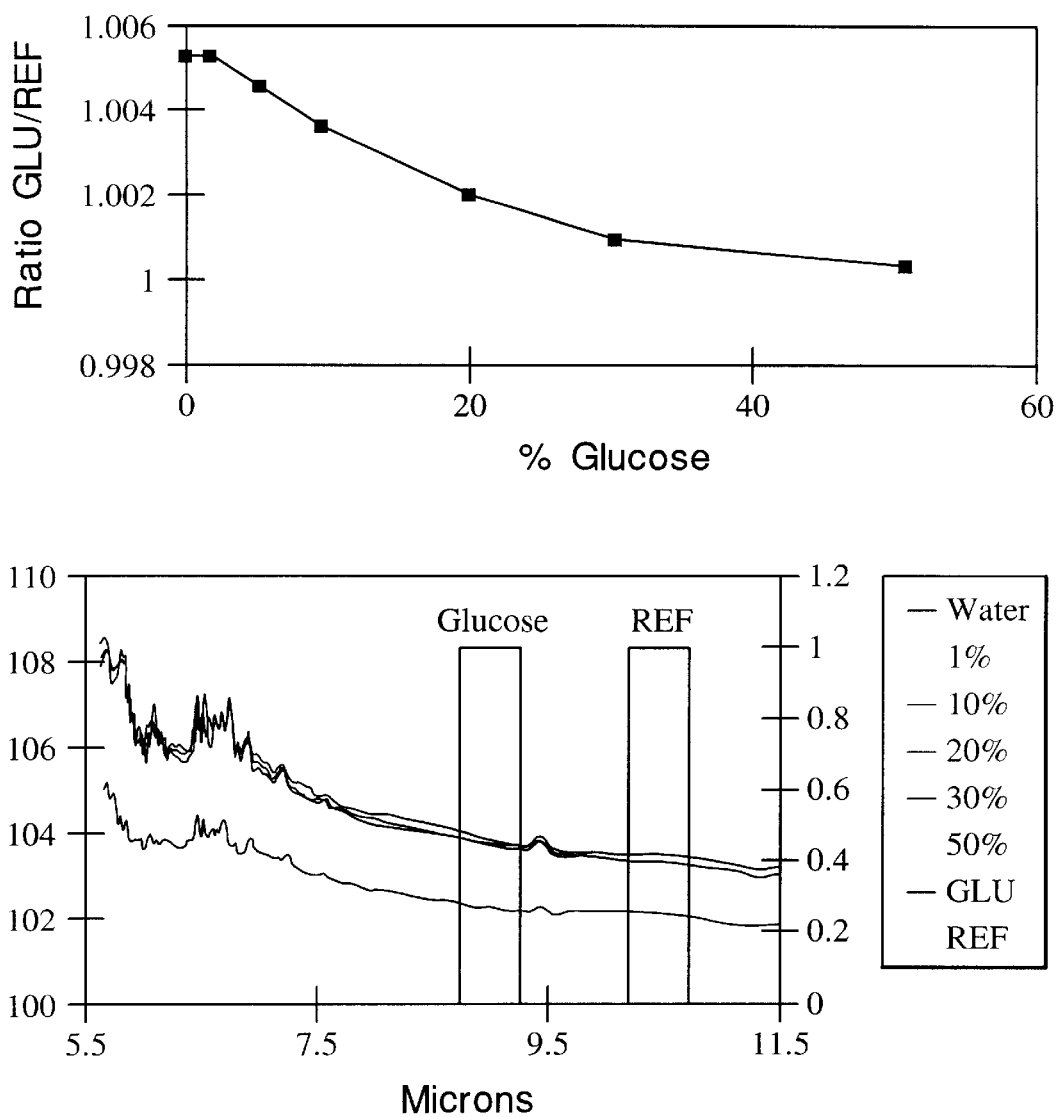
FIG. 6 contains two graphs showing the ratio of analytical band energy/reference band energy vs. Constituent concentration and the analytical and reference bands superimposed on the infrared energy spectra in accordance with FIG. 3.

The ratio of analytical band energy/reference band energy is plotted vs. Constituent concentration in the curve shown in FIG. 6. The upper portion of this figure shows the relationship between the emitted energy ratios and the concentration of the analyte. The lower portion of the figure shows the emitted energy vs. wavelength for several concentrations of glucose and the glucose and reference analytical bands used. Those skilled in the art will recognize this relationship as Beer's Law.

$$I = Io * exp - x\, c\, a$$

Where:
I=energy detected
Io=energy emitted
x=path length
c=number of absorbing molecules
a=absorption constant It is not necessary to explicitly measure x (path length) to use this technique to compute useful glucose concentrations. For example, metabolic glucose concentrations are expressed in mg/dL or milligrams of glucose per 100 milliliter of fluid. Thus, what is actually required is not an absolute measurement of glucose molecules but a ratio of glucose to other fluid molecules per unit volume.

The technique presented here can be used to measure water, proteins, and glucose. Examination of the absorption spectra reveal that water has characteristic absorption bands near 6.1 and 12 microns, proteins absorb from 6.0 to 8.4 microns and glucose absorbs from 8.5 to 10.0 microns. Using these absorption bands one can compute the relative concentration of each species by ratioing. The ratio of glucose to water yields a representation of glucose in mg/dl.

To more clearly understand the operation of the present invention in the context of a particular embodiment or embodiments, refer now to the following discussion.

In a first embodiment, a natural occurring thermal gradient like that described above in the context of a human body is utilized. That is, the temperature gradient is such that the temperature is cooler at a location within the body closer to the detector (i.e. the surface temperature of the skin is 30 degrees C.) than at a more distant location (i.e. the interior skin layer 37 degrees C.).

Figure 7:
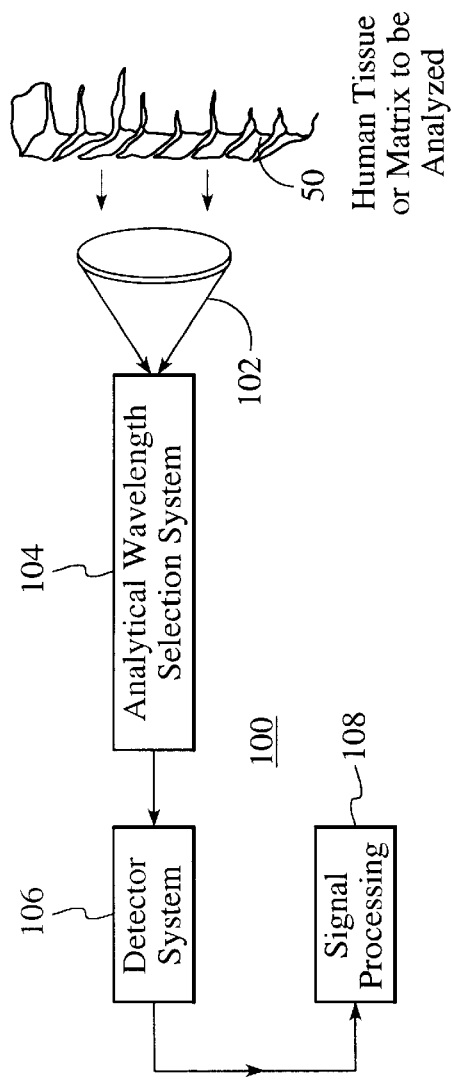
FIG. 7 is a first embodiment of a spectrometer in accordance with the present invention.

Referring now to FIG. 7, what is shown is a first embodiment of such a system 100. In this embodiment, infrared emissions from the body 50 are collected by an optical collector 102. A particular wavelength is selected that corresponds to a particular constituent in the body 50, by a wavelength selection system 104. A detector 106 receives information from the selection system 104. A signal processing system 108 processes the information. The various elements of the system will be described herein below.

Analytical Wavelength Selection System 104

Several means of selecting the analytical wavelengths can be used such as:

Discrete infrared bandpass filters

An interferometer

A spectrophotometer

A grating monochrometer

A variable filter monochrometer

In the preferred embodiment a set of 9 discrete analytical filters manufactured by Optical Coating Laboratories Inc. (Santa Rosa, Calif.) are used. In an alternate embodiment a PERKIN ELMER (England) System 2000 Fourier Transform Infra Red Spectrophotometer (FTIR) is used in place of the filters. The filters provide a compact system that is rugged and relatively economical. The use of a specific set of bandpass filters restricts the instrument to analyzing only pre selected wavelengths. The use of the FTIR allows the optical measurements of all wavelengths. When using an FTIR the final analysis wavelengths are selected in the signal processing computer. Therefore an instrument built with discrete filters is dedicated to measuring a predetermined compound, e.g. glucose, while an instrument built using an FTIR can be directed via software modifications to measure any of a number of compounds such as glucose, alcohol, etc.

Detector System 106

The detector system converts the infrared energy into usable electrical signals. The detector system 106 typically comprises of two components, an infrared detector and a preamplifier.

In the preferred embodiment the detector is an array of 9 Photo Voltaic Mercury Cadmium Telluride (PVMCT) detectors. A detector such as a FERMIOINICS (Simi Valley, Calif.) model PV-9.1 with a PVA-481-1 pre-amplifier is acceptable. Similar units from other manufacturers such as GRASEBY (Tampa, Fla.) can be substituted.

Signal Processing System 108

The signal processing system 108 used in the preferred embodiment is a personal computer (PC) manufactured by Digital Equipment Corp. (DEC) model 4331px. Others can be substituted. The computer provides a computation engine, display and user interface to the system. An A/D converter system manufactured by Strawberry Tree, Inc. (STI) in San Jose, Calif., model "WORKMATE PC" is used to interface the analog signals from the detector to the computer.

In the alternate configuration using the FTIR the Perkin Elmer instrument incorporates a GRASEBY 1×1 MCT detector and includes a computer interface so the Fermionics and STI devices are not required to complete the system.

Figure 8:
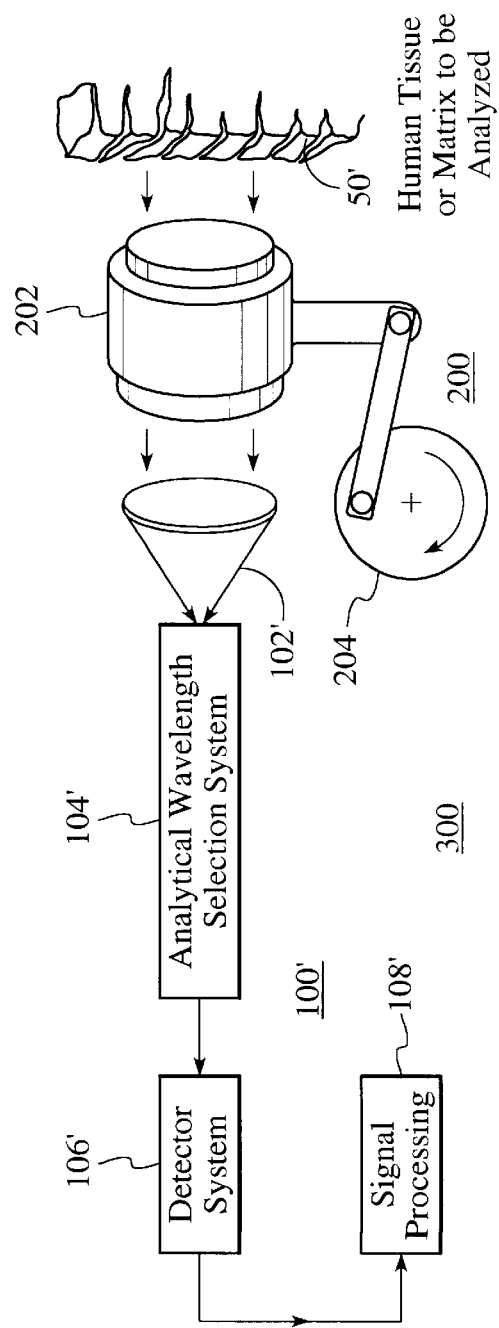
FIG. 8 is a second embodiment of spectrometer in accordance with the present invention.

Referring now to FIG. 8, what is shown is a general block diagram of a second embodiment of a system in which a temperature gradient is enhanced or induced in the body to clearly establish a temperature differential. The system 300 includes similar components to those shown in system 100 except system 300 includes a thermal gradient inducer 200 for inducing a temperature gradient within the body. The inducer 200 includes chilling mechanism 202, which repeatedly contacts the body 50' through a reciprocating mechanism 204.

In a preferred embodiment, the chilling mechanism 202 is brought in contact with a body. Also in a preferred embodiment, the chilling mechanism is a chilled germanium crystal. The germanium material allows the infrared energy to pass through the chilling mechanism and in to the optical collector while still contacting the body and enhancing the temperature gradient. Utilizing this system after each contact of the chilling mechanism with the body 50' an optical measurement is made by the system 100' and the measurements averaged over several contact cycles.

Chilling Mechanism 202

In a preferred embodiment the chilling mechanism 202 is a germanium crystal which is manufactured by Meller Optics of Providence, RI. It is 1.91 cm diameter and 0.75" long. Both end surfaces are "polished to optically flat condition". Other materials, geometries and sizes are acceptable. The crystal's function is twofold. One is to cool the measurement "site", and the other is to efficiently collect and transmit the infrared energy to the collector and detector systems.

The germanium crystal is chilled by a water cooling jacket to approximately 10 Deg. C. This temperature provides an enhanced temperature gradient at the measurement site to enhance the infrared signal to allow detection by conventional detectors. The cooling jacket is typically a water jacket connected to a water bath such as a LAUDA model RM-20. The water bath is operated at 10 Deg. C. and the bath's internal circulating pump circulates water inside the jacket to cool the crystal. Alternately the crystal can be cooled with a thermo-electric cooler such as Mellcor (Trenton, N.J.) FCO.6 controlled by an Alpha Instruments (Johnston, RI) TEC controller. Additional means for cooling the target surface include cold N2 or other gases, infrared transmissive cooling fluids circulated immediately in contact with target window rear surface.

Since the temperature of the crystal surface is below the dew point special precautions must be taken to assure that no condensation exists on any surface through which infrared energy is collected. This necessitates either dehumidified enclosures, mechanical defrosting of the crystal surfaces or chemical means for dew prevention.

After the germanium crystal contacts the measurement site the proper gradients exist for approximately 500 ms. After that time the crystal is removed and the site re-warmed.

Reciprocating Mechanism 202

In a preferred embodiment, movement of the crystal is accomplished by a cam and lever mechanism driven by a gear head motor such as a MicroMo Inc. (St. Petersburg, Fla.) model 2842S. Other mechanisms could be substituted. The requirement is only that the crystal be moved 0.32 cm to 0.64 cm away from the skin to allow re-warming.

Re-Warming can be accomplished passively by just letting the body re-warm itself by means of local blood flow to the measurement site. Initial body surface temperatures are typically 30 Deg. C. and after 500 ms of chilled crystal contact the skin surface cools to about 20 Deg. C. Natural re-warming will take approximately 15 seconds. Alternately the re-warming can be accelerated by blowing warm air at the measurement site or bringing the measurement site in contact with a warm conductive surface.

The surface or air temperature should not exceed 50 Deg. C. to avoid discomfort. Optical methods of re-warming by directing infrared, UV or visible light at the measurement site are also applicable. Alternate re-warming means may include ultrasound or microwave. Unlike the cooling means the re-warming mechanism of the present invention need not be infrared transmissive since no signals are measured during the re-warming phase of the cycle. The time of contact with or exposure to the re-warming source is determined by the time required to raise the temperature of the target site tissue from the cooled temperature, to approximately 41 Deg. C.

After the surface has been re-warmed to between 30 and 40 Deg. C. the measurement cycle can be repeated. In the preferred embodiment approximately 100 cycles constitute a determination of blood glucose level.

When the crystal is in contact with the patient's skin infrared energy in the 3 to 15 micron band passes from the skin through the crystal and into the dispersive element of the system. The purpose of the dispersive element is to select analytical wavelengths. With the proper wavelengths selected the computation of glucose concentrations based on the theory described above can be accomplished. A typical operating sequence is shown below.

Operating Sequence

Step 1. Bring instrument in contact with patient's forearm.

Step 2. Reciprocating mechanism brings chilled crystal in contact with patient's skin for 500 ms Step 3. Optical energy is detected, selected, and analyzed by the system signal processor to determine glucose concentration per the algorithm discussed above.

Step 4. Reciprocating mechanism removes crystal from skin.

Step 5. Skin re-warms.

Step 6. After skin has re-warmed to approximately 30 to 40 Deg. C. the cycle is repeated until 100 separate glucose determinations have been made.

Step 7. Average all 100 measurements and report result.

The useful range of analytical wavelengths of the present invention is wide. In a sample at room temperature (25 Deg. C.) the peak energy emissions are at 9.8 microns. In the case of a human body (maintained typically at 37 Deg. C.) the peak emissions are near 9.3 microns. Substances at other temperatures have peak emissions at other wavelengths. In the case of room temperature or human body temperature samples the analytical range containing most of the energy is from 2 to 14 microns. Energy levels outside of that band are very low. To use the technique in shorter wavelength bands the sample can be heated.

Although the present invention has been described in accordance with the embodiments shown in the figures, one of ordinary skill in the art recognizes there could be variations to the embodiments and those variations would be within the spirit and scope of the present invention. For example, the body to be analyzed could be human skin, agricultural products, packaged goods, manufactured products or any other liquid and/or solid body and their use would be within the spirit and scope of the present invention. Similarly, the infrared measuring device can be a variety of instruments including but not limited to FTIR Spectrophotometer, Multi Element MCT Detector Array, infrared detector with Filter Wheel, and Thermopile Detector Array with individual Filters and their use would be within the spirit and scope of the present invention.

Additionally, modifications of the thermal gradient mechanism operation can be envisioned to shorten the time sequenced heating and cooling operations to approach a near steady state gradient condition by means of co-axial or off axis injection of optical, laser or microwave energy to effect deep tissue heating concurrently with surface cooling and IR energy collection by the germanium crystal. Control of the depth profile of a steady-state gradient is effected by the depth of heat penetration, e.g. wavelength selection, vs. the cooling conditions established at the surface.

Finally, many different constituents could be analyzed including but not limited to concentrations of glucose, concentrations of alcohol, concentrations of other body components, presence of substances such as drugs and their analysis would be within the spirit and scope of the present invention. Accordingly, many modifications may be made by one of ordinary skill in the art without departing from the spirit and scope of the present invention, the scope of which is defined by the appended claims.

We claim:

1. A method for noninvasive infrared absorption spectrometry comprising:
    (a) inducing a temperature gradient in a body such that the temperature is cooler on the surface than internally;
    (b) measuring the intensity and wavelength of infrared energy emanating from within the body by multiple sequential measurements taken at predetermined times; the body having a temperature gradient that is warmer inside the body than on a surface of the body;
    (c) utilizing the detected infrared energy for analysis of at least one constituent of the body; the utilizing step further including the steps of:
        (c1) quantifying the infrared energy in a band known to be absorbed by the at least one constituent;
        (c2) quantifying the infrared energy in a band known to be not absorbed by the at least one constituent; and
        (c3) calculating the amount of the infrared energy absorbed by the at least one constituent based on the steps (c1) and (c2).

2. The method of claim 1 in which the body comprises a solid.

3. The method of claim 2 in which the body comprises a human body.

4. The method of claim 2 in which the body comprises a liquid.

5. The method of claim 2 in which the at least one constituent comprises glucose.

6. A noninvasive thermal gradient subsurface absorption spectrometer comprising:
    means for inducing a temperature gradient in a body such that the temperature is cooler on the surface than internally and such that the temperature gradient propagates to multiple predetermined depths of the body at predetermined times;
    means for measuring the intensity and wavelength of infrared energy emanating from within the body by multiple sequential measurements taken at predetermined times; the body having a temperature gradient that is warmer inside the body than on a surface of the body;
    means for utilizing the detected infrared energy for analysis of at least one constituent of the body; the utilizing means further including:
        first means for quantifying the infrared energy in a band known to be absorbed by the at least one constituent;
        second means for quantifying the infrared energy in a band known to be not absorbed by the at least one constituent; and
    means for calculating the amount of energy absorbed by the at least one constituent based on the first and second quantifying means, the calculating means determining the concentration of the at least one constituent at different depths within the body at multiple sequential predetermined time.

7. The spectrometer of claim 6 in which the body comprises a solid.

8. The spectrometer of claim 6 in which the body comprises a human body.

9. The spectrometer of claim 6 in which the body comprises a liquid.

10. The spectrometer of claim 6 in which the at least one constituent comprises glucose.

11. A noninvasive thermal gradient subsurface absorption spectrometer comprising:
    a cooling means for controllably reducing a surface temperature of a body to cause the thermal gradient to have magnitude, propagation velocity, and contour profile that maximizes spectral content of an infrared energy passing through and absorbed by subsurface layers of the body that contain concentrations of at least one constituent of interest;
    means for measuring the intensity and wavelength of infrared energy emanating from with the body by multiple sequential measurements taken at predetermined times; the body having a temperature gradient that is warmer inside the body than on a surface of the body;
    means for utilizing the measured infrared energy for analysis of at least one constituent of the body; the utilizing means further including:
        first means for quantifying the infrared energy in a band known to be absorbed by the at least one constituent;
        second means for quantifying the infrared energy in a band known to be not absorbed by the at least one constituent; and
    means for calculating the amount of the infrared energy absorbed by the at least one constituent based on the first and second quantifying means, the calculating means being performed at multiple sequential predetermined times to calculate the concentration of the at least one constituent at different depths within the body.

12. The spectrometer of claim 11 in which the body comprises a solid.

13. The spectrometer of claim 11 in which the body comprises a human body.

14. The spectrometer of claim 11 in which the body comprises a liquid.

15. The spectrometer of claim 11 in which the at least one constituent comprises glucose.

16. A noninvasive thermal gradient subsurface absorption spectrometer comprising:

cooling means for controllably reducing a surface temperature of a body after the body temperature has been artificially raised to create a gradient whose magnitude, propagation velocity and contour profile maximize the spectral content of a infrared absorption spectra of a plurality of layers of the body containing the concentrations of the constituent of interest;

means for measuring the intensity and wavelength of infrared energy emanating from within the body by multiple sequential measurements taken at predetermined times; the body having a temperature gradient that is warmer inside the body than on a surface of the body;

means for utilizing the detected infrared energy for analysis of at least one constituent of the body; the utilizing means further including:

first means for quantifying the infrared energy in a band known to be absorbed by the at least one constituent;

second means for quantifying the infrared energy in a band known to be not absorbed by the at least one constituent; and means for calculating the amount of the infrared energy absorbed by the at least one constituent based on the first and second quantifying means, the calculating means being performed at multiple sequential predetermined times to calculate the concentration of the at least one constituent at different depths within the body.

17. The spectrometer of claim 16 in which the body comprises a solid.

18. The spectrometer of claim 16 in which the body comprises a human body.

19. The spectrometer of claim 16 in which the body comprises a liquid.

20. The spectrometer of claim 16 in which the at least one constituent comprises glucose.

21. An apparatus for noninvasive subsurface infrared spectrometry comprising:

means for alternately heating and cooling a surface of a heterogeneous body to establish a thermal gradient whose magnitude, propagation velocity and depth profile maximize a spectral content of infrared energy from a plurality of layers within the heterogeneous body; optical means to collect a maximum amount of the energy coaxially with the alternately heating and cooling means;

wavelength selection means for receiving the energy from the optical means that is synchronized with the spectral content of infrared energy detected from deep layers of the plurality of layers as the thermal gradient propagates through the body;

a detector system for converting the spectral content of the infrared energy into electrical signals;

a signal processor means for converting the electrical signals into measures of concentration of a constituent of interest within the deep layers; the signal processor means including means for utilizing the detected infrared energy for analysis of at least one constituent of the body; the utilizing means further including:

first means for quantifying the infrared energy in a band known to be absorbed by the at least one constituent;

second means for quantifying the infrared energy in a band known to be not absorbed by the at least one constituent; and means for calculating the amount of infrared energy absorbed by the at least one constituent based on the first and second quantifying means, the calculating means being performed at multiple sequential predetermined times to calculate the concentration of the at least one constituent at different depths within the body.

22. The spectrometer of claim 21 in which the body comprises a solid.

23. The spectrometer of claim 21 in which the body comprises a human body.

24. The spectrometer of claim 21 in which the body comprises a liquid.

25. The spectrometer of claim 21 in which the at least one constituent comprises glucose.

26. A noninvasive thermal gradient subsurface spectrometer comprising:

means for inducing a temperature gradient in a body such that a temperature is cooler on a surface of the body than internally and such that the temperature gradient propagates to multiple predetermined depths of the body at predetermined times;

means for measuring the intensity and wavelength of infrared energy emanating from with the body; the body having a temperature gradient that is warmer inside the body than on a surface of the body by multiple sequential measurements taken at predetermined times;

means for utilizing the measured infrared energy for analysis of at least one constituent of the body; the utilizing means further including:

first means for quantifying the infrared energy in a band known to be absorbed by the at least one constituent;

second means for quantifying the infrared energy in a band known to be not absorbed by the at least one constituent; and means for calculating the amount of the infrared energy absorbed by the at least one constituent based on the first and second quantifying means, the calculating means being performed at multiple sequential predetermined times to calculate the concentration of the at least one constituent at different depths within the body.

27. The spectrometer of claim 26 in which the body comprises a solid.

28. The spectrometer of claim 26 in which the body comprises a human body.

29. The spectrometer of claim 26 in which the body comprises a liquid.

30. The spectrometer of claim 26 in which the at least one constituent comprises glucose.

31. An apparatus for noninvasive subsurface infrared absorption spectrometry comprising:

means for alternately heating and cooling a heterogeneous body to establish a thermal gradient whose magnitude and contour profile maximize a spectral content of infrared absorption of deep layers of the heterogeneous body;

an optical means to collect a maximum amount of the spectral content of the infrared absorption coaxially with the alternately heating and cooling means; means for measuring the intensity and wavelength of infrared energy emanating from within the body; the body having a temperature gradient that is warmer inside the body than on a surface of the body by multiple sequential measurements taken at predetermined times;

a wavelength selection means for receiving an infrared absorption spectral content of the optical means that is synchronized with the spectral content of the infrared absorption provided from the deep layers as the thermal gradient stabilizes through the layers;

means for converting the synchronized spectral content of infrared absorption into electrical signals; and means for utilizing the converted infrared energy for analysis of at least one constituent of the body; the utilizing means further including:

first means for quantifying the infrared energy in a band known to be absorbed by the at least one constituent;

second means for quantifying the infrared energy in a band known to be not absorbed by the at least one constituent; and means for calculating the amount of the infrared energy absorbed by the at least one constituent based on the first and second quantifying means, the calculating means calculating the concentration of the at least one constituent at different depths within the body at multiple sequential predetermined times.

32. The spectrometer of claim 31 in which the body comprises a solid.

33. The spectrometer of claim 31 in which the body comprises a human body.

34. The spectrometer of claim 31 in which the body comprises a liquid.

35. The spectrometer of claim 31 in which the at least one constituent comprises glucose.

36. A method for noninvasive thermal gradient subsurface absorption spectrometry comprising the steps of:

(a) inducing a temperature gradient in a body such that a temperature is cooler on the surface than internally and such that the temperature gradient propagates to multiple predetermined depths of the body at predetermined times;

(b) measuring the intensity and wavelength of infrared energy emanating from within a body by multiple sequential measurements taken at predetermined times; the body having a temperature gradient that is warmer inside the body than on a surface of the body;

(c) utilizing the measured infrared energy for analysis of at least one constituent of the body; the utilizing step further including:

(c1) quantifying the infrared energy in a band known to be absorbed by the at least one constituent;

(c2) quantifying the infrared energy in a band known to be not absorbed by the at least one constituent; and (c3) calculating the amount of the infrared energy absorbed by the at least one constituent based on the steps (c1) and (c2), the calculating step being performed at multiple sequential predetermined times to calculate the concentration of the at least one constituent at different depths within the body.

37. The method of claim 36 in which the body comprises a solid.

38. The method of claim 36 in which the body comprises a human body.

39. The method of claim 36 in which the body comprises a liquid.

40. The method of claim 36 in which the at least one constituent comprises glucose.

41. A method for noninvasive thermal gradient absorption subsurface spectrometry comprising the steps of:

(a) controllably reducing a surface temperature of a body to cause the thermal gradient to have magnitude, propagation velocity, and contour profile that maximizes spectral content of an infrared energy passing through and absorbed by subsurface layers of the body that contain concentrations of at least one constituent of interest;

(b) measuring the intensity and wavelength of infrared energy emanating from within the body by multiple sequential measurements taken at predetermined times; the body having a temperature gradient that is warmer inside the body than on a surface of the body;

(c) utilizing the measured infrared energy for analysis of at least one constituent of the body; the utilizing step further including:

(c1) quantifying the infrared energy in a band known to be absorbed by the at least one constituent;

(c2) quantifying the infrared energy in a band known to be not absorbed by the at least one constituent; and (c3) calculating the amount of the infrared energy absorbed by the at least one constituent based on steps (c1) and (c2), the calculating step being performed at multiple sequential predetermined times to calculate the concentration of the at least one constituent at different depths within the body.

42. The method of claim 41 in which the body comprises a solid.

43. The method of claim 41 in which the body comprises a human body.

44. The method of claim 41 in which the body comprises a liquid.

45. The method of claim 41 in which the at least one constituent comprises glucose.

46. A method for noninvasive thermal gradient subsurface absorption spectrometry comprising the steps of:

(a) reducing a surface temperature of a body after the body temperature has been artificially raised to create a gradient whose magnitude, propagation velocity and contour profile maximize a spectral content of the infrared absorption spectra of a plurality of layers of the body containing concentrations of the constituent of interest;

(b) measuring the intensity and wavelength of infrared energy emanating from within the body by multiple sequential measurements taken at predetermined times; the body having a temperature gradient that is warmer inside the body than on a surface of the body; and (c) utilizing the measured infrared energy for analysis of at least one constituent of the body; the utilizing step further including:

(c1) quantifying the infrared energy in a band known to be absorbed by the at least tone constituent;

(c2) quantifying the infrared energy in a band known to be not absorbed by the at least one constituent; and (c3) calculating the amount of the infrared energy absorbed by the at least one constituent based on steps (c1) and (c2), the calculating step being performed at multiple sequential predetermined times to calculate the concentration of the at least one constituent at different depths within the body.

47. The method of claim 46 in which the body comprises a solid.

48. The method of claim 46 in which the body comprises a human body.

49. The method of claim 46 in which the body comprises a liquid.

50. The method of claim 46 in which the at least one constituent comprises glucose.

51. A method for noninvasive subsurface infrared absorption spectrometry comprising the steps of:
   (a) sequentially heating and cooling a surface of a heterogeneous body to establish a thermal gradient whose magnitude, propagation velocity and depth profile maximize the spectral content of infrared energy from layers within the heterogeneous body, the body including a plurality of layers;
   (b) collecting a maximum amount of the energy of the spectral content coaxially with the sequentially heating and cooling step;
   (c) receiving the energy that is synchronized with the spectral content of the infrared energy detected from deep layers of the plurality of layers as the thermal gradient propagates through the layers;
   (d) converting the spectral content infrared energy into electrical signals;
   (e) converting the electrical signals into measures of concentration of the constituent of interest within the deep layers by quantifying the infrared energy absorbed in a cooler layer, the converting step further including;
      (e1) quantifying the infrared energy in a band known to be absorbed by the at least one constituent;
      (e2) quantifying the infrared energy in a band known to be not absorbed by the at least one constituent; and
      (e3) calculating the amount of the infrared energy absorbed by the at least one constituent based on step (e1) and (e2), the calculating step being performed at multiple sequential predetermined times to calculate the concentration of the at least one constituent at different depths within the body.

52. The method of claim 51 in which the body comprises a solid.

53. The method of claim 51 in which the body comprises a human body.

54. The method of claim 51 in which the body comprises a liquid.

55. The method of claim 51 in which the at least one constituent comprises glucose.

56. A method for noninvasive thermal gradient subsurface absorption spectrometry comprising the steps of:
   (a) inducing a temperature gradient in a body such that the temperature is cooler on a surface of the body than internally and such that the temperature gradient propagates to multiple predetermined depths of the body at predetermined times; and
   (b) measuring the intensity and wavelength of infrared energy emanating from within the body by multiple sequential measurements taken at predetermined times; the body having a temperature gradient that is warmer inside the body than on a surface of the body;
   (c) utilizing the detected infrared energy for analysis of at least one constituent of the body; the utilizing step further including:
      (c1) quantifying the infrared energy in a band known to be absorbed by the at least one constituent;
      (c2) quantifying the infrared energy in a band known to be not absorbed by the at least one constituent; and
      (c3) calculating the amount of the infrared energy absorbed by the at least one constituent based on steps (c1) and (c2), the calculating step being performed at multiple sequential predetermined times to calculate the concentration of the at least one constituent at different depths within the body.

57. The method of claim 56 in which the body comprises a solid.

58. The method of claim 56 in which the body comprises a human body.

59. The method of claim 56 in which the body comprises a liquid.

60. The method of claim 56 in which the at least one constituent comprises glucose.

61. A method for noninvasive subsurface infrared absorption spectrometry comprising the steps of:
   (a) alternately heating and cooling a heterogeneous body to establish a thermal gradient whose magnitude and contour profile maximize the spectral content of infrared absorption of deep layers of the heterogeneous body;
   (b) collecting a maximum amount of the spectral content of the infrared absorption coaxially with the alternately heating and cooling step;
   (c) measuring the intensity and wavelength of infrared energy emanating from within the heterogeneous body by multiple sequential measurements taken at predetermined times; the heterogeneous body having a temperature gradient that is warmer inside the body than on a surface of the body;
   (d) receiving the infrared absorption spectral content of the collecting step that is synchronized with the spectral content of the infrared absorption provided from the deep layers as the thermal gradient stabilizes through the layers;
   (e) converting the synchronized spectral content of infrared absorption into electrical signals; the converting step further including:
      (e1) quantifying the infrared energy in a band known to be absorbed by at least one constituent of the body;
      (e2) quantifying the infrared energy in a band known to be not absorbed by the at least one constituent; and
      (e3) calculating the amount of the infrared energy absorbed by the at least one constituent based on steps (e1) and (e2), the calculating step being performed at multiple sequential predetermined times to calculate the concentration of the at least one constituent at different depths within the body.

62. The method of claim 61 in which the body comprises a solid.

63. The method of claim 61 in which the body comprises a human body.

64. The method of claim 61 in which the body comprises a liquid.

65. The method of claim 61 in which the at least one constituent comprises glucose.

66. A noninvasive infrared spectrometer comprising:
   detector means for measuring the intensity and wavelength of infrared energy emanating from within a body; the body having a temperature gradient that is warmer inside the body than on a surface of the body;
   means for inducing a temperature gradient in a body such that the temperature is cooler on the surface than internally; the inducing means comprising a chilling system; the chilling system further comprising:
      a chilling mechanism;

an optical path defrosting means; and a reciprocating mechanism coupled to the chilling mechanism, the reciprocating mechanism for causing the chilling mechanism to come into contact with the body to induce the temperature gradient therein.

67. A noninvasive infrared spectrometer comprising:

detector means for measuring the intensity and wavelength of infrared energy emanating from within a body; wherein the body comprises a solid or a liquid, the body having a temperature gradient that is warmer inside the body than on a surface of the body;

means for inducing a temperature gradient in a body such that the temperature is cooler on the surface than internally; the inducing means comprising a chilling system; the chilling system further comprising:

a chilling mechanism; and a reciprocating mechanism coupled to the chilling mechanism, the reciprocating mechanism for causing the chilling mechanism to come into contact with the body to induce the temperature gradient therein.

\* \* \* \* \*